United States Patent
Powell et al.

(10) Patent No.: US 9,842,197 B2
(45) Date of Patent: Dec. 12, 2017

(54) ATHLETE INFORMATIONAL DEVICE

(71) Applicants: Douglas C Powell, Charlotte, NC (US); Carolyn F Humphrey, Charlotte, NC (US); John G Humphrey, Alexandria, VA (US); Corey L. Reil, Platte City, MO (US)

(72) Inventors: Douglas C Powell, Charlotte, NC (US); Carolyn F Humphrey, Charlotte, NC (US); John G Humphrey, Alexandria, VA (US); Corey L. Reil, Platte City, MO (US)

( * ) Notice: Subject to any disclaimer, the term of this patent is extended or adjusted under 35 U.S.C. 154(b) by 239 days.

(21) Appl. No.: 14/793,738

(22) Filed: Jul. 7, 2015

(65) Prior Publication Data
US 2017/0007883 A1    Jan. 12, 2017

(51) Int. Cl.
| | |
|---|---|
| G06F 7/32 | (2006.01) |
| G06F 19/00 | (2011.01) |
| G06F 9/54 | (2006.01) |
| G07C 1/22 | (2006.01) |
| G06Q 50/22 | (2012.01) |

(52) U.S. Cl.
CPC .......... *G06F 19/3481* (2013.01); *G06F 9/542* (2013.01); *G06Q 50/22* (2013.01); *G07C 1/22* (2013.01)

(58) Field of Classification Search
CPC .............................. G06F 19/3481; G06F 9/542
See application file for complete search history.

(56) References Cited

U.S. PATENT DOCUMENTS

| | | | |
|---|---|---|---|
| 5,578,353 A | 11/1996 | Drew, III | |
| 6,042,881 A | 3/2000 | Ewan | |
| 6,964,229 B1 * | 11/2005 | Zimmerman | B41K 1/02 101/109 |
| 7,865,394 B1 | 1/2011 | Calloway | |
| 8,322,059 B2 * | 12/2012 | Henshaw | G09F 3/10 40/586 |
| 8,649,890 B2 * | 2/2014 | Martin | G06F 19/3481 700/91 |
| 9,578,914 B2 * | 2/2017 | Fierro | A42B 1/12 |
| 2003/0055831 A1 * | 3/2003 | Ryan | G06F 17/3061 |
| 2004/0152454 A1 | 8/2004 | Kauppinen | |
| 2006/0016358 A1 * | 1/2006 | Zimmerman | B41K 1/02 101/483 |
| 2013/0088005 A1 | 4/2013 | Henshaw | |

* cited by examiner

*Primary Examiner* — Joshua T Kennedy

(57) ABSTRACT

A digital image with athletic information organized on it to be output to a computer, smartphone and/or physical, including adhesive-backed textiles that remain adhesive and retain ink when water or perspiration is present in the environment, paper, and other media.

8 Claims, 3 Drawing Sheets

ATHLETE INFORMATIONAL DEVICE

RELATED APPLICATION

This application is a continuation of previously filed U.S. application Ser. No. 62/021,250 filed Jul. 7, 2014, all hereby incorporated by reference in their entirety.

TECHNICAL FIELD

The present invention is in the technical field of athletics. More particularly, the present invention is in the technical field of athletic information devices.

BACKGROUND OF INVENTION

Coaching received by the athlete is typically verbal, though it can be written, while a formal evaluation, if given, can be electronically provided or via letter or written word. These are then either remembered or not, journaled or not, during the course of the practices in between competition events and worked on to varying degrees based on a number of factors, including memory, stress, commitment, motivation, distractions or other outside factors. As such, comments by coaches get lost or forgotten while, in other cases it can cause athletes to spend more team thinking about too much rather than focusing on the few things that provide the most improvement opportunities.

Conventional athletic competition information devices such as heat sheets are typically available at athletic competitions or meets and are produced prior to the event in order to provide information to athletic competitor, parents and coaches regarding the events in which each athlete is competing, the heat (sub group of the overall group that is competing in, say, Freestyle or Backstroke in swimming, a weight class in wrestling, or the 400-meter run in track), the lane or match in which they will actually compete as well as their entry time or other qualifying criteria, which is a measure of how well that athlete has previously performed in that event (often in minutes and/or seconds).

An athletic competition takes place in its appropriate venue (e.g., swim meets take place at a pool) and is comprised of events featuring one particular discipline within the sport or events featuring several or all disciplines (e.g., track meets feature many disciplines, swim meets feature many or all disciplines). Each athletic competition is attended by athletes of differing age groups or other classifications such as weight or size (e.g., martial artists and/or wrestlers generally compete in a class or experience group). Generally, athletes in each group or classification compete against each other and the boys compete against boys in their same group or classification and girls compete against girls in their same group or classification. Mathematically, based on the number of lanes in a pool or on a track or other areas of competition and the number of athletes competing in a particular discipline, athletes are divided into "heats" or "matches" (e.g., a pool with 5 lanes with 50 swimmers for an age group would have 10 heats of 5 swimmers each). They are first seeded by their entry time or other qualifying criteria, which is generally the fastest historical time or best performance in which that athlete has performed in that event.

Each discipline is assigned an "event number" (e.g., in swimming, Girls 10 & Under 50-Meter Backstroke could be event #5, while the Boys equivalent could be event #6). Each athlete is then assigned a lane or location (for example, lane or ring 1, 2, 3. 4 or 5) for the discipline and heat or match in which she or he is competing. They are then timed either by electronic or stopwatch to determine how fast they can complete the event (e.g., a 10 year old girl might finish Event #5, Girls 10 & Under 50 Meter Backstroke in 45 seconds) or judged for points scored (e.g., a wrestler in a particular weight class scores a certain number of points for performing certain moves successfully).

Finally, many sports governing bodies provide motivational goals for athletes. For example, USA Swimming, the governing body for competitive swimming in the United States, utilizes a specific formula every four years, coinciding with the Summer Olympic swimming competition, to reset the "motivational times" it publishes for swimmers in each age group based upon that the times achieved by swimmer's in that year's Summer Olympics. These "motivational times" are meant to help swimmers of a particular age group progress as they get older both within their group and as they move from one age group to the next. (For example, following the 2012 Olympics, a 10-year old girl whose best historical time in the 50-Meter Backstroke is 45 seconds would have a "BB" time under the USA Swimming motivational time regime because her time would be faster than the "BB" time mark of 49.59 seconds and slower than the "A" time mark of 43.49 seconds. Such a swimmer would then aspire to get an "A" time by swimming faster than 43.49 seconds in a future meet.)

In most athletic competitions, the event number, order of the events, best historical times or scores, and motivational times or goals are provided in a "heat sheet" or similar program that is prepared by the meet sponsors. A "heat sheet" typically lists all of the events in order and within each heat or match lists the athletes who will compete in each event. The athlete, parent, or spectator buys the heat sheet or program, hunts through the pages to find the relevant event/heat/larie or location information, uses a marker to draw and fill out a grid on the heat sheet with the athlete's information and/or on the athlete's arm or leg for the athlete to reference throughout the competition. For a multi-day meet, there would be multiple permanent ink grids on an athlete's body. Meet officials also use heat sheets to keep track of each event.

The following information contained in a heat sheet is maintained in a sports event management system that tracks who is competing and her or his age or other classification, team, and best time or score in the event to determine how the athlete should be seeded or ordered. Heat sheets themselves are simply print outs or electronic copies of the data organized for the meet. There are other devices on which information can be written for athletes, parents, supporters and meet officials to inform them about the details of the events, and there are applications that display the above information in various electronic formats on computers and/or smartphones. Heat sheets can and do often get lost (or wet being around swimmers/pools), and athletic competitors cannot always have an electronic device handy to check the information.

A pre-printed temporary tattoo requires access to water, towels, etc. as well as introduces operational challenges to the athletic club to implement their use. Temporary tattoos require the actions to complete. During the assembly process, errors are common due its manual nature, creating waste and causing the tattoos not to stick properly. The amount of work inherent in performing the various temporary tattoo functions is burdensome and very difficult to scale to large volumes of athletes, especially given the volunteer nature of most athletic clubs.

Further, in between an athlete's events it is often unclear as to the amount of time to elapse before the athlete's next event. During this time, athletes and parents try to determine the need for warm up or warm down, nutritional consumption and/or alternative uses of that time to help drive mental and physical relaxation, enjoyment or recuperation.

Many sports have a multiple-event format including swimming, wrestling, track and field, karate and others. Swimming and track meets have events, heats and lanes. Karate and wrestling meets include multiple match locations in single or multiple venues, making it important for participants and their fans to know when and where events take place.

SUMMARY OF THE INVENTION

The present invention is a digital image with the competition specific information for each athletic competitor organized in a way that makes it easily readable and able to be output to various electronic devices or on physical media.

DETAILED DESCRIPTION OF EMBODIMENTS

Figures 1, 2:
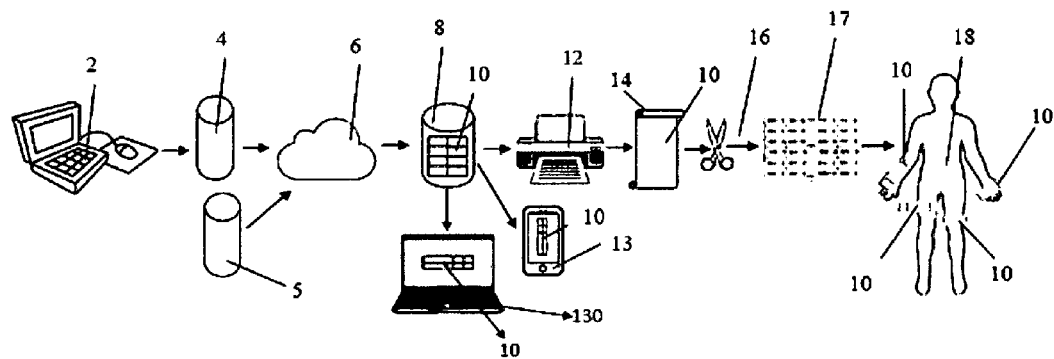
FIG. 1 is the process for creating the athletic information digital image of the present invention
FIG. 2 is front view of the athletic information digital image of the present invention.

Referring now to the invention in more detail, in FIG. 1 there is shown a high level process for creating the athletic information digital image 10. The sports event management system 2, which is not part of the invention, creates an athletic competition data export file 4 of the sports event data, which was anticipated by Zimmerman (US Patent Application Publication 2006/0016358, Par. 0019-0020, 0022, 0025) and is also not a part of this invention. The athletic competition data export file 4 contains each athlete's name 20, events 42. competed in, heats 48 or matches within each event to which the athlete 18 is assigned, the lane 15 or location to which the athlete 18 is assigned for each heat 48 or match, the athlete's 18 best historical time 56 or score in the event, and, for a multi-day athletic competition, the day of the event 24. The coaching and motivational data file 5 is a data file compiled as part of the invention from multiple data sources. The coaching and motivational data file 5 does not include any information stored in the athletic competition data export file 4.

The coaching and motivational data file 5 includes data and information contained in FIG. 2 such as motivational times 62, letter designators 60, comments or tips 124 by the athlete's coach to enhance the athlete's 18 performance for each event 42 in which the athlete 18 will compete in an athletic competition; motivational times 62 and letter designator 60 appropriate to the sport and competitions the athlete competes in, such as the USA Swimming motivational time and letter designation for each event 42 in which a swimmer will compete in a swim meet; the athlete's team logo 96; information identifying the athlete's team colors and directing the athletic information digital image 10 to print using the team colors; inspirational and motivational images; and other motivational information identified for and associated with each athlete. In the context of an athletic competition in which an athlete will compete in various events 42 with time delay in-between the events, the cloud-based data processing system 6 also calculates an approximate wait time 131 displayed next to the wait time label 104 between the events in the athletic competition from the information contained in the athletic competition management system 2.

The athletic competition data export file 4 and coaching and motivational data file 5 are consumed by our cloud-based data processing system 6, which identifies, collects, analyzes, and compiles into the athletic information digital image file 8 the desired data from the athletic competition data export file 4, the coaching and motivational data file 5, and, in the context of a multi-event athletic competition, the results of the calculation of approximate wait times 131 between events associated with each athlete. Through this process, the athletic information digital image file 8 contains a unique set of data for each athlete 18. The information in the athletic information digital image file 8 then is exported to generate a athletic information digital image 10 for each athlete.

Once the athletic information digital image 10 is generated, it can be output in any of several methods depending on consumer preference. An individual athletic information digital image 10 could be transmitted via text to a smart phone 13 with image viewing capabilities, transmitted to an email address to be viewed on a computer or smart phone, or transmitted via the internet to be viewed on a computer 130 or smart phone 13. An individual athletic information digital image 10 also could be reversed and printed via a printer 12 onto physical paper 14 or other transfer media, then cut or trimmed via a cutting device 16 and adhered to the athlete 18 in a desired, visible location.

If the desired output is a physical media 14 such as an adhesive-backed textile paper or tattoo medium, a single output file for an individual athlete or multiple output files 8 can be created. In the context of an athletic competition when multiple output files 8 are created for output to a physical media 14 such as an adhesive-backed textile paper or temporary tattoo medium, the athletic information digital images 10 are organized by teams competing in a meet or competition first and then within each team organized in alphabetical or reverse alphabetical order. The athletic information digital images 10 then are arranged into vertical columns of reversed athletic information digital images 10, with three columns per printed physical media 14 such as an adhesive-backed textile paper or temporary tattoo medium. Once printed, the athletic information digital images 10 are cut utilizing any of many available commercial and retail cutting devices and stored for transport and distribution in the file binder 17. Finally, the file binder 17 is used at the athletic competition to track and distribute the printed athletic information digital images 10.

As those skilled in the art of coaching or competing in athletic events would realize that the information on the athletic information digital image will need to be readable throughout the entire event. Hence it is important in the physical paper 14 or document to ensure that ink received from the printer 12, is retained on the paper in the presence of water or perspiration coming into contact with the printed physical media such as adhesive backed textile based paper or tattoo media.

Referring now to the invention in more detail, in FIG. 2 there is shown an athletic information digital image 10 set up for an athletic competition. A similar athletic information digital image 10 with corresponding information specific to a particular sport would be set up in a similar fashion. The athletic information digital image 10 in this embodiment is comprised of information compiled from the athletic competition data export file 4, the coaching and motivational data file 5, and wait times 131 calculated from data in the athletic competition data export file 4. The athletic information digital image 10 is made up of rows Name Row 28, heading row 66 and one to many detail rows 70 that provide different pieces of information for a swimmer to use. Additionally, and depending on whether the operator chooses to include wait times 131 in the digital image, there may be an additional row 100 containing the wait time 131, which is the period of time calculated to pass between the completion of one identified event and the start of the next identified event. The inclusion of wait time 131 allows for athletes and parents to make informed choices regarding warm up/warm down, nutrition, relaxation, etc.

The first row 28 contains the athlete's full name 20 and, optionally for an athletic competition lasting more than one day—a multi-day meet—a cell for the Image Day 22 and three character Image Day Abbreviation 24, or the day of the meet to which the image refers (e.g., SAT for Saturday, SUN for Sunday, MON for Monday, etc.). If the meet is only one day or, if the operator does not include multi-day information, the cell Image Day 22 and the Image Day Abbreviation 24 will not be present.

The heading row 66 is not optional. The Event Cell 30 contains the word "Event" 74. Under the Event Cell 30, the event name cells 68 and Event Name 42 will appear.

The E header cell 32 contains the event abbreviation of "E" under which the Event Cell 46 and Event Number 44 will show for each row 70 included for a swimmer. The H header cell 34 contains the Heat abbreviation "H" under which the heat cell 50 and heat number 48 assigned to the swimmer for an event number 44 will appear. The L header cell 36 contains the Lane abbreviation "L" under which the lane cell 54 and lane number 52 for each event number 44 will appear.

The entry header cell 38 contains the word "Time" under which the Entry Cell 58 and a time previously completed 56 for each event number 44 will appear. The Goal header cell 40 shows the word "Goal" or another reference under which the goal cell 72, goal motivational time 62 and, because this example is set up for a swimming competition, the USA Swimming motivational letter designation 60 for each event number 44 will appear. In a different sport, other motivational goals would be substituted here. In this set-up for a swimming event, the goal header cell 40, goal cell 72 and goal motivational time 62 USA Swimming motivational letter designation 60 are optional.

In more detail, still referring to FIG. 2, and depending on the preferences specified in the cloud based system 6 in FIG. 1, a wait time row 100 will show before each event number 44 to be competed in. The wait time 131 comes from the cloud based system 6 in FIG. 1. The wait time row 100 would show the approximate wait time 131 provided by the cloud based system 6, from FIG. 1.

The cells in the heading row 66 including cells 30, 32, 34, 36, 38 and 40 may be of any particular color and the font for the text in 30, 32, 34, 36, 38 and 40 may be of any particular color. The event number 44 can be up to three digits. The heat number 48 can be up to three digits. The lane number 52 can be up to three digits. The entry time 56 and goal time 62 can be up to two digits for minute and second. The accuracy of the entry time 56 and goal time 62 will be to the hundredth of a second.

In more detail, still referring to the invention of FIG. 2, the event name 42, event number 44, heat number 48, lane number 52 and entry time 56 will be provided in the heat sheet file 4 generated by the swim meet management system 2, which is not managed by this invention. The motivational goal information, in this example the USA Swimming motivational time 62 and USA Swimming motivational letter designation 60 will be drawn from the coaching and motivational data file 5 by the cloud based system 6.

In further detail, still referring to the invention of FIG. 2 the athletic information digital image 10 as well as cells 20, 22, 24, 68, 46, 50, 58 and 72 will be of sufficient width to house the information. Only for the participant name cell 20 will the information for first name be truncated in the event of a long name. The base height of the athletic information digital image 10 depends on the number of event rows 28, the preferences selected at image generation and the output device and/or media.

The construction details of the invention as shown in FIG. 1 are that the athletic information digital image 10.

Figures 3, 4:
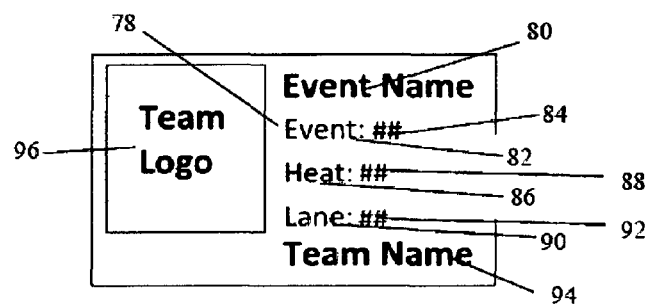
FIG. 3 is the front view of an alternate version of the athletic information digital image with coach's comments.
FIG. 4 is the front view of an additional alternate version of the athletic information digital image in which a team's logo appears.

Referring now to an additional feature of the invention shown as an alternative design in FIG. 3. The athletic information digital image 10 from FIG. 1 is shown with a different option selected in the cloud based system 6 also from FIG. 1. The athletic information digital image 10 in this embodiment is comprised of information compiled from both the athletic competition data export file 4 and the coaching and motivational data file 5. If the option to include coach's comments 124 is chosen on the cloud based system 6 from FIG. 1, the athletic information digital image 10 in this embodiment would look as follows. The elements name row 28, swimmers full name 20, Heading Row 66, Event Cell 30, "Event" 74, Detail Row 70, Event Name Cell 68, Event Name 42, Event Cell 46, Event Number 44, E Header Cell 32, H Header Cell 34, Heat Number 48, Heat Cell 50, L Header Cell 36, Lane Number 52 and Lane Cell 54 the same as designated in FIG. 2.

FIG. 3 shows an alternate version of the athletic information digital image 10 that includes a coach's comment 124. The Envision Cell 120 contains the words "Envision This . . . ", under which the Coaching Cell 122 and coach's Comment 124 appear for each Event Number 44 for an athlete. In the alternative version shown in FIG. 3, the entry header cell 38, the entry cell 58 and best previous time or score 56 elements are replaced with Coaching Cell 122 and coach's comment 124. The coach's comment 124 is derived from coaching and motivational data file 5.

Referring now to another possible alternative design of the invention shown in FIG. 4 is the athletic information digital image 10 from FIG. 1 with the event name 80 showing near the top. The athletic information digital image 10 in this embodiment is comprised of information compiled from both the athletic competition data export file 4 and the coaching and motivational data file 5. The team logo 96, is on the left side of the athletic information digital image 78. The event label 82 and the event number 84 are listed immediately below the event name 80. Under the event label 82 and event number 84 are the lane label 90 and lane number 92. Finally, under the lane label 90 and lane number 92 is the team name graphic 94.

The team logo 96 and team graphic 94 are derived from coaching and motivational data file 5. The event label 82, event number 84, lane label 90, and lane number 92 are derived from the athletic competition data export file 4.

The advantages of the present invention include, without limitation, that the information is in a far more accessible and comprehensible format during an athletic practice or athletic competition than a workout list, heat sheet, or other program provided to an athlete, the athlete's family, or the athlete's supporters in a format that was not either digital or printed on a non-adhesive substrate that did not retain its adhesiveness or the readability of the ink used in an environment in which water or perspiration is present; allows coaches and others to provide coaching tips and other information to encourage and focus the athlete on particular ways to perform at her or his best; allows the athletic competitor, family and supporters to more easily understand the athlete's events 74 on a particular day, and when a time 56 has been lowered/improved and a goal has been reached; reduces the amount of paper used to print heat sheets at meets; allows the parents and athletes to know in an easier fashion in what set of events, heats and lanes or locations in which they compete without having to write this information on the athlete's body in permanent ink; allows meet officials to more easily identify athletes and assist them in queuing up and participating in the correct event and heat or match; allows coaches and others to provide coaching tips and other information to encourage and focus the athlete on particular ways to perform at her or his best; and allows the athletic competitor, family and supporters to more easily understand when a time has been lowered/improved and a goal has been reached.

Figure 5:
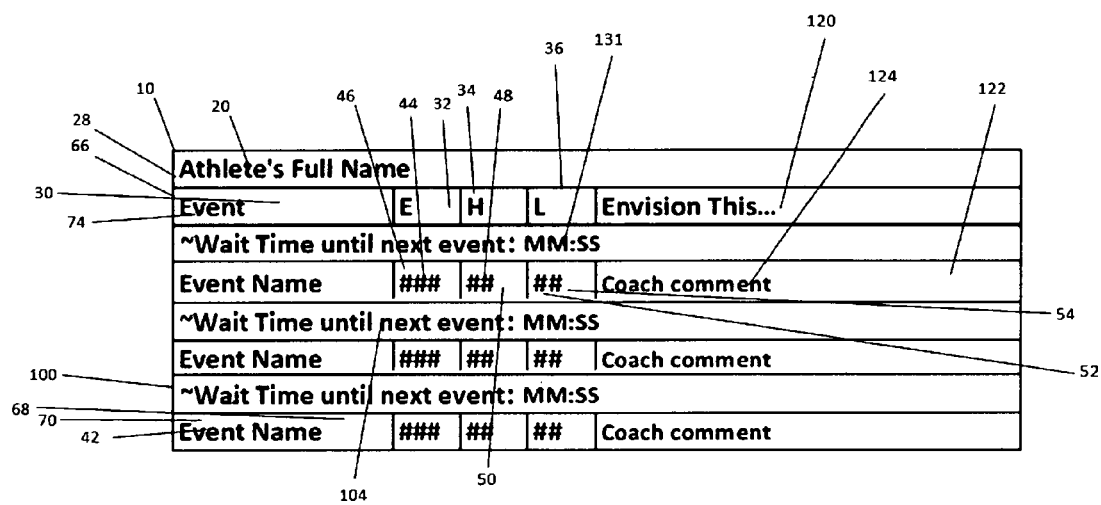
FIG. 5 is the front view of an additional alternate version of the athletic information digital image in which both the optional coach's comment and optional calculated wait time appear.

Referring now to an additional feature of the invention shown as an alternative design in FIG. 2 and FIG. 3. FIG. 5 shows an alternate version of the athletic information digital image 10 that includes a coach's comment 124 and the calculated wait time 131 displayed next to the wait time label contained in the optional wait time row 100. The Envision Cell 120 contains the words "Envision This . . . ", under which the Coaching Cell 122 and coach's comment 124 appear for each Event Number 44 for an athlete. In the alternative version shown in FIG. 3, the entry header cell 38, the entry cell 58 and best previous time or score 56 elements are replaced with Coaching Cell 122 and coach's comment 124. The coach's comment 124 is derived from coaching and motivational data file 5.

The present invention described below is an improvement over previous inventions. At least one other method is the creation of a blank grid using a stamp, applying it to the skin and then writing or drawing swim information from the heat sheet manually onto the grid. U.S. Pat. No. 6,964,229—Method for recording multi-event sports meet information on skin—Terri Chassay "T. C." Zimmerman, claims a method using an ink stamp to imprint the grid on the skin and then to manually write the information onto the grid. This patent also describes but does not claim the use of a tattoo for the purpose of creating the grid to which information would be added. The present invention improves upon this earlier invention by creating a digital image that could be disseminated through a variety of electronic and physical media, including temporary tattoos, and incorporating into that image a wide variety of logistical and motivational information directly into the digital image.

Other patents deal with taking sports information and adhering it to the skin. U.S. Pat. No. 5,578,353—Tattoo admission ticket—James H. Drew, Ill. U.S. Pat. No. 5,578,353; which discusses the use of temporary tattoos to identify someone having paid admission to an event. U.S. Pat. No. 8,322,059—athletic information display—describes the incorporation of particular athletic information into a temporary tattoo that displays particular information about a running event including a map of the race and goal times at different stages of the race. The present invention innovates beyond and improves upon these patents by creating a digital image that can be disseminated through a variety of electronic and physical media including temporary tattoos, by creating a process for collecting and processing a wide array of information to be included in the digital image, and by being sufficiently flexible to be applicable to competitions across a wide range of athletic disciplines.

In broad embodiment, the present invention is the organization of an athlete's events, names, event numbers, heats or matches, lanes or locations, entry and, optionally, motivational times/letters, coach's comments, team colors and logos/other images organized into a digital image for visual consumption by a customer.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention.

We claim:

1. A method by which a coach can motivate, guide and enhance the performance of an athlete by creating an athletic information digital image to support the athlete comprising the following steps:
   a. Inputting motivational information, comprising coach's comments and motivational times, into a coaching and motivational data file that is specific to each athlete;
   b. identifying, collecting, analyzing and compiling information for each athlete from a respective coaching and motivational data file and integrating the motivational information into the athletic information digital image;
   c. integrating information from an athletic competition management system about an event order, an event location, and a time of an event in an athletic competition into the athletic information digital image;
   d. calculating and integrating into the athletic information digital image an approximate wait time between events in the athletic competition calculated from information stored in the athletic competition management system;
   e. rendering the athletic information digital image, containing the aggregated information resulting from integrating the data identified, collected, analyzed, and compiled from the coaching and motivational data file, the athletic competition management system, and the wait time data calculated from the athletic competition management system, into a format configured to be disseminated via electronic transmission or printing onto a physical media;
   f. printing the athletic information digital image on an adhesive-backed textile-based paper that:
      i. does not lose its adhesiveness to an athlete's skin when an athlete's skin is in contact with water or perspiration;
      ii. will receive an ink and then, in the presence of water or perspiration in an athletic environment, will retain the ink;

g. surface cutting a sheet of the adhesive-backed textile-based paper so that a section of the sheet containing the printed athletic information digital image can be separated from other sections of the sheet containing other instances of the printed athletic information digital image;

h. distributing the section of the sheet of the adhesive-backed textile-based paper containing the printed athletic information digital image to the athlete; and i. applying the section of the sheet of adhesive-backed textile-based paper containing the printed athletic information digital image to the athlete by removing the adhesive-backed textile-based paper from the sheet protecting it and placing the adhesive side of the paper in contact with the skin of the athlete.

2. The method of claim 1, further comprising providing the athletic information digital image comprising the transmission of the image electronically to the athlete, a family member of the athlete, and a supporter of the athlete.

3. The method of claim 2 where the athletic information digital image is embedded in and transmitted electronically via a software application using a Multimedia Messaging Service message without an accompanying alphanumeric text message embedded in the Multimedia Messaging Service message.

4. The method of claim 2 where the athletic information digital image is embedded in and transmitted electronically via a software application using the Multimedia Messaging Service message with the accompanying alphanumeric text message embedded in the Multimedia Messaging Service message.

5. The method of claim 2 where the athletic information digital image is transmitted and displayed by means of a software application on a mobile communications device or a personal computer.

6. The method of claim 2 where the athletic information digital image is embedded in and transmitted electronically via a software application using e-mail.

7. The method of claim 1, further comprising the athletic information digital image the motivational data input and stored in the coaching and motivational data file and the approximate wait time between the athlete's events in the athletic competition.

8. The method of claim 1, further comprising the athletic information digital image the coach's comments input and stored in the coaching and motivational data file and the approximate wait time between the athlete's events in the athletic competition.

* * * * *